US009414745B2

(12) United States Patent
Neice (10) Patent No.: US 9,414,745 B2
(45) Date of Patent: Aug. 16, 2016

(54) PUPILLOMETRY SYSTEMS, METHODS, AND DEVICES

(71) Applicant: Andrew Elliott Neice, Lake Oswego, OR (US)

(72) Inventor: Andrew Elliott Neice, Lake Oswego, OR (US)

( * ) Notice: Subject to any disclaimer, the term of this patent is extended or adjusted under 35 U.S.C. 154(b) by 40 days.

(21) Appl. No.: 14/590,477

(22) Filed: Jan. 6, 2015

(65) Prior Publication Data

US 2016/0192837 A1    Jul. 7, 2016

Related U.S. Application Data

(60) Provisional application No. 61/935,845, filed on Feb. 5, 2014.

(51) Int. Cl.
*A61B 3/10* (2006.01)
*A61B 3/11* (2006.01)
*A61B 3/00* (2006.01)
*A61B 3/14* (2006.01)

(52) U.S. Cl.
CPC ............... *A61B 3/112* (2013.01); *A61B 3/0025* (2013.01); *A61B 3/1005* (2013.01); *A61B 3/145* (2013.01)

(58) Field of Classification Search
CPC .................................. A61B 3/13; A61B 3/112
USPC .................... 351/204, 205, 246, 221
See application file for complete search history.

(56) References Cited

U.S. PATENT DOCUMENTS 7,083,280 B2 * 8/2006 Hakamata ................ A61B 3/11
351/200

OTHER PUBLICATIONS

NPi—200, Neuroptics Pupillometer, Product available at www.neuroptics.com.
De Souza, John Kennedy Schettino, et al., An open-source, FireWire camera-based, Labview-controlled image acquisition system for automated, dynamic pupillometry and blink detection, Computer Methods and Programs in Biomedicine, Dec. 2013, pp. 607-623, vol. 112, Issue 3, available at http://www.sciencedirect.com/science/article/pii/S0169260713002460.
Maz Warga et al., How do Spontaneous Pupillary Oscillations in Light Relate to Light Intensity?, Vision Research, Feb. 2009, pp. 295-300, vol. 49, Issue 3, available at http://www.sciencedirect.com/science/article/pii/S0042698908004689.
Anne-Claire et al., The Relevance of Pupillometry for Evaluation of Analgesia Before Noxious Procedures in the Intensive Care Unit. 2015, available at http://journals.lww.com/anesthesia-analgesia/Abstract/publishahead/The_Relevance_of_Pupillometry_for_Evaluation_of.98342.aspx.
B Wilhelm et al., Pupillographic Assessment of Sleepiness in Sleep-Deprived Healthy Subjects, Sleep 12.3, May 1998, pp. 258-265, available at http://www.pubfacts.com/detail/9595604/Pupillographic-assessment-of-sleepiness-in-sleep-deprived-healthy-subjects.

* cited by examiner

*Primary Examiner* — Hung Dang
(74) *Attorney, Agent, or Firm* — Mohr Intellectual Property Law Solutions, PC (57) ABSTRACT

Pupillometry systems for measuring one or more pupillary characteristics of a patient are shown and described. The puillometry systems include at least one camera for capturing image data of one or more pupils, at least one radiation source configured to project radiation to the one or more pupils, and a computer system in data communication with the at least one camera, the computer system having a processor and a non-transitory computer-readable storage medium. The non-transitory computer-readable storage medium includes computer-readable instructions for collecting and time stamping the image data, identifying and measuring the one or more pupils in the image data, processing the image data to produce measurement data of change in the one or more pupillary characteristics, and calculating a standardized output of measurement data for the one or more pupillary characteristics.

20 Claims, 6 Drawing Sheets

PUPILLOMETRY SYSTEMS, METHODS, AND DEVICES

CROSS REFERENCE TO RELATED APPLICATIONS

This application claims priority to and the benefit under 35 U.S.C. §119(e) of copending U.S. Provisional patent application Ser. No. 61/935,845, filed on Feb. 5, 2014, which is hereby incorporated by reference for all purposes.

BACKGROUND

The present disclosure relates generally to pupillometry systems, methods, and devices. In particular, pupillometry systems and methods that automatically calculate a standardized output value that can be used by an operator for medical diagnosis are described.

Changes in the pupil can occur as a result of medications, drugs, and/or toxins (e.g., cough and cold medications, anticholinergic drugs, benzodiazepines, amphetamines, cocaine, lysergic acid diethylamide, marijuana, other narcotics, poisonous mushrooms, belladonna, chloroform, etc.). Pupil changes caused by medications, drugs and toxins are generally temporary. In addition to causing changes in size and response, drugs and/or toxins may affect a characteristic known as pupillary unrest, which is the variation in pupil size about its mean. Determining pupil size, pupillary unrest, pupillary response, and/or other pupillary characteristics can be useful in determining the presence and/or type of medications drugs, and/or toxins in the system of a patient. Further, changes in pupil size and unequal pupil size can be indicators of other serious conditions such as head trauma, brain tumors, and/or stroke. Thus, measuring pupil size and responses can be important for appropriate treatment for a patient.

Devices that measure the radius, diameter, circumference, or other characteristics of a pupil are generally referred to as pupillometers, and the analysis of these measurements is referred to as pupillometry. Pupillometry has a wide variety of applications. For example, precise measurements of pupil size may be useful in planning surgery or other procedures on the eye. Abnormal changes in pupil size, or failure of pupil size to change in response to stimuli (i.e., fixed pupils) may indicate that the patient has a neurological injury. Changes in the pupil size with time (i.e., pupillary unrest) can be correlated with drowsiness. It may additionally correlate with consumption of certain pharmaceuticals, and pupillary unrest may be useful in determining the activity of these pharmaceuticals.

Known pupillometers are not entirely satisfactory for the range of applications in which they are employed. For example, it can be difficult to assess pupillary unrest using only the data provided by a conventional pupillometer, which is typically reported as pupil diameter versus time. This can be difficult for several reasons. First, the amplitude of the variation is often quite small and difficult to appreciate, particularly when there are ongoing changes in the baseline pupil diameter, or noise in the system. Secondly, the operator may be unfamiliar with the frequencies generally associated with pupillary unrest, and may mistake variations in pupil size that are too high or too low in frequency to be clinically relevant with clinically important pupillary unrest. Lastly, the frequency of the pupil variation may change slightly during the measurement and confuse the operator.

In addition, known pupillometers report pupillometry data as size versus time, with no analysis of frequency components. This is only marginally useful if the user wishes to appreciate the frequency components of the pupillometry data. One technique for analyzing the frequency components is application of a Fourier transform. The Fourier transform changes data that is in the form of amplitude versus time to the form of amplitude versus frequency. A Fourier transform makes the amplitude of various frequency components apparent and can therefore be useful in interpreting pupillary unrest from pupillometry data. The Fourier transform is itself, however, difficult for an inexperienced operator to interpret. An inexperienced operator is unlikely to be aware of what frequency range is relevant to different clinical situations and/or how to correctly interpret frequency data.

Thus, there exists a need for pupillometry systems, methods, and devices that improve upon and advance the design of known pupillometers. Examples of new and useful pupillometry systems, methods, and devices relevant to the needs existing in the field are discussed below.

Disclosure addressing one or more of the identified existing needs is provided in the detailed description below. Examples of references relevant to pupillometers include U.S. Patent References: U.S. Pat. No. 3,782,364, U.S. Pat. No. 5,784,145, U.S. Pat. No. 7,625,087, and U.S. Pat. No. 8,127,882. The complete disclosures of the above patents are herein incorporated by reference for all purposes.

SUMMARY

The present disclosure is directed to pupillometry systems for measuring one or more pupillary characteristics of a patient. The puillometry systems include at least one camera for capturing image data of one or more pupils, at least one radiation source configured to project radiation to the one or more pupils, and a computer system in data communication with the at least one camera, the computer system having a processor and a non-transitory computer-readable storage medium. The non-transitory computer-readable storage medium includes computer-readable instructions for collecting and time stamping the image data, identifying and measuring the one or more pupils in the image data, processing the image data to produce measurement data of change in the one or more pupillary characteristics, and calculating a standardized output of measurement data for the one or more pupillary characteristics.

DETAILED DESCRIPTION

The disclosed pupillometry systems, methods, and devices become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various pupillometry systems, methods, and devices are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

With reference to FIGS. 1-6, a first example of a pupillometry system, system 200, will now be described. Pupillometry system 200 allows for an operator 202 to collect and analyze pupillometry data collected from a patient 204. Specifically, pupillometry system 200 functions to collect, process, and analyze puillometry data from patient 204 and display a standardized output of pupillometry data to operator 202. Additionally or alternatively, system 200 can be used to diagnose the patient or determine the presence and/or type of medications, drugs, or toxins that may have been consumed by the patient.

Figure 2:
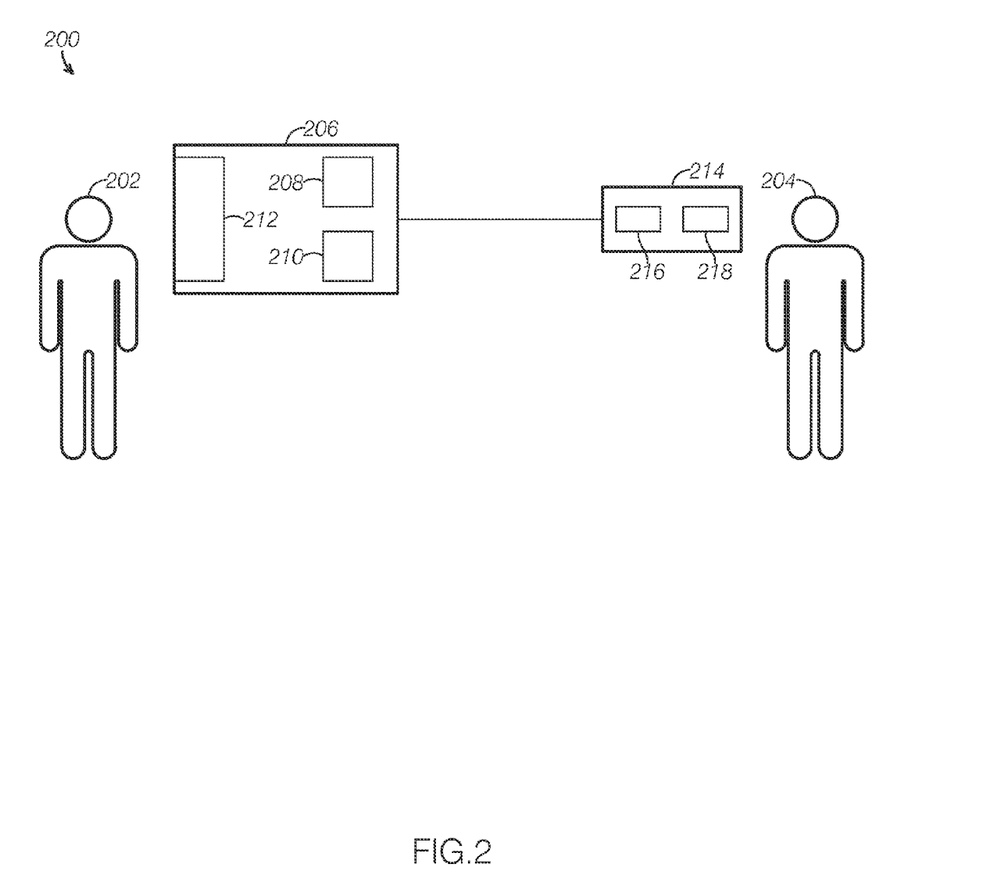
FIG. 2 is a schematic view of a first example pupillometry system including a programmable computing device, such as the example device shown in FIG. 1.

System 200 includes a computer system 206 having at least a non-transitory computer-readable storage medium 208, a processor 210, and a display 210. System 200 further includes a positioning device 214 for positioning a radiation source 216 and a camera 218 in a position to project light into and capture image data from one or more of the pupils of the patient.

Pupillometry system 200 addresses many of the shortcomings existing with conventional pupillometers. For example, the presently described system rapidly collects image data for pupil dimensions as a function of time. In another example, the system of the present application analyzes the frequency and amplitude of oscillations of pupil size, generates a standardized output of the magnitude of these oscillations by calculating the area under the curve of the Fourier transform in a band of clinically relevant frequencies, and displays the data and/or standardized output to the operator. Additionally or alternatively, the system may be capable of measuring additional characteristics of the pupil (e.g., pupillary constriction or dilation in response to changing light stimulus, average pupil diameter in the dark or light, pupil to iris ratio in the dark or light, etc.), displaying measurements of the additional pupillary characteristics, and/or calculating and displaying ratios of these measurements. The operator can then use the displayed data to make clinical decisions regarding diagnosis, prognosis, and/or medication dosing.

Various disclosed examples may be implemented using electronic circuitry configured to perform one or more functions. For example, with some embodiments of the invention, the disclosed examples may be implemented using one or more application-specific integrated circuits (ASICs). More typically, however, components of various examples of the invention will be implemented using a programmable computing device executing firmware or software instructions (i.e., computer-readable instructions), or by some combination of purpose-specific electronic circuitry and firmware or software instructions (i.e., computer-readable instructions) executing on a programmable computing device.

Figure 1:
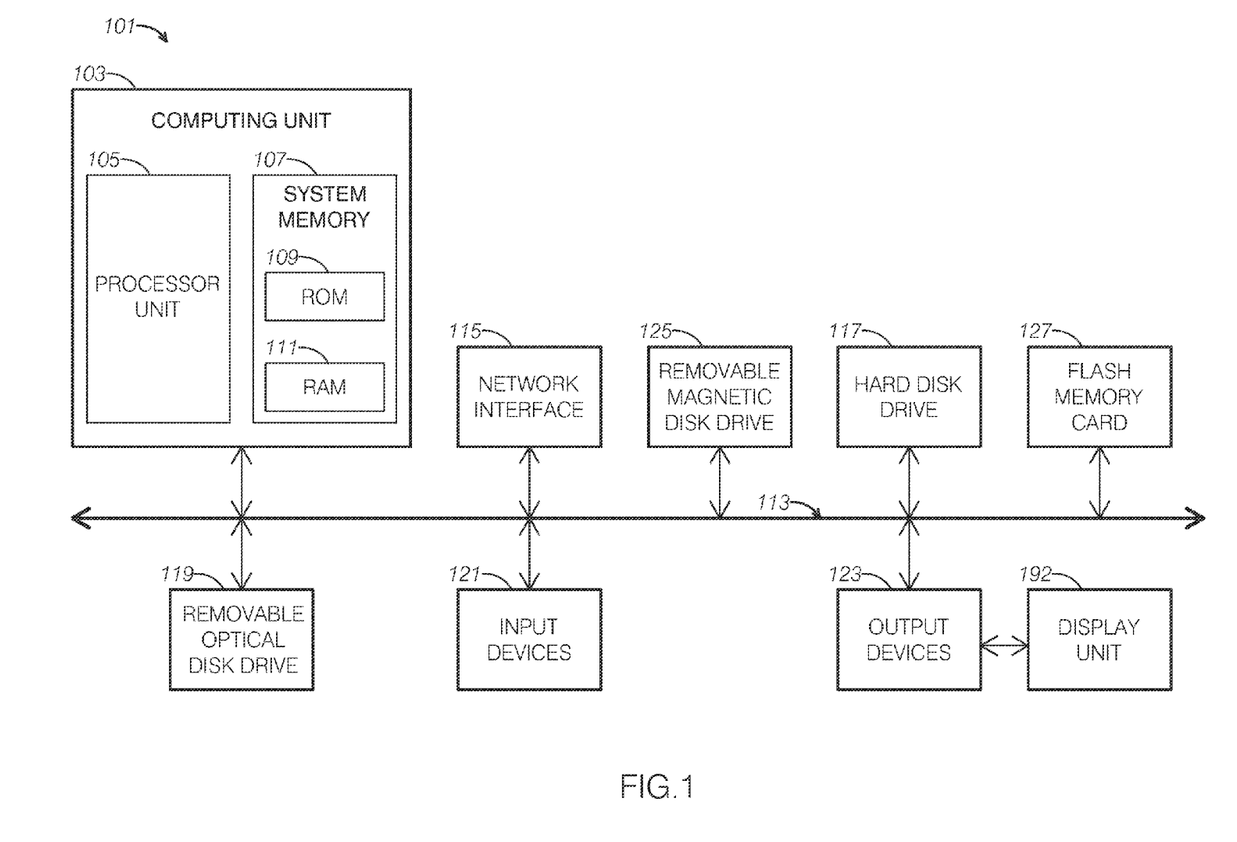
FIG. 1 is a schematic view of an example of a programmable computing device.

Accordingly, FIG. 1 shows one illustrative example of a computer, computer 101, which can be used to implement various embodiments of the invention. Computer 101 may be incorporated within a variety of consumer electronic devices, such as personal media players, cellular phones, smart phones, personal data assistants, global positioning system devices, and the like.

As seen in this figure, computer 101 has a computing unit 103. Computing unit 103 typically includes a processing unit 105 and a system memory 107. Processing unit 105 may be any type of processing device for executing software instructions (i.e., computer-readable instructions), but will conventionally be a microprocessor device. System memory 107 may include both a read-only memory (ROM) 109 and a random access memory (RAM) 111. As will be appreciated by those of ordinary skill in the art, both read-only memory (ROM) 109 and random access memory (RAM) 111 may store software instructions to be executed by processing unit 105.

Processing unit 105 and system memory 107 are connected, either directly or indirectly, through a bus 113 or alternate communication structure to one or more peripheral devices. For example, processing unit 105 or system memory 107 may be directly or indirectly connected to additional memory storage, such as a hard disk drive 117, a removable optical disk drive 119, a removable magnetic disk drive 125, and a flash memory card 127. Processing unit 105 and system memory 107 also may be directly or indirectly connected to one or more input devices 121 and one or more output devices 123. Input devices 121 may include, for example, a keyboard, touch screen, a remote control pad, a pointing device (such as a mouse, touchpad, stylus, trackball, or joystick), a scanner, a camera or a microphone. Output devices 123 may include, for example, a monitor display, an integrated display, television, printer, stereo, or speakers.

Still further, computing unit 103 will be directly or indirectly connected to one or more network interfaces 115 for communicating with a network. This type of network interface 115 is also sometimes referred to as a network adapter or network interface card (NIC). Network interface 115 translates data and control signals from computing unit 103 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 115 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof. For example, the computer 101 may be connected to a digital music player, such as an IPOD® brand digital music player or iOS or Android based smartphone. As known in the art, this type of digital music player can serve as both an output device for a computer (e.g., outputting music from a sound file or pictures from an image file) and a storage device.

In addition to a digital music player, computer 101 may be connected to or otherwise include one or more other peripheral devices, such as a telephone. The telephone may be, for example, a wireless "smart phone," such as those featuring the Android or iOS operating systems. As known in the art, this type of telephone communicates through a wireless network using radio frequency transmissions. In addition to simple communication functionality, a "smart phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with computer 101 so that their data maintained may be synchronized.

Of course, still other peripheral devices may be included with or otherwise connected to a computer 101 of the type illustrated in FIG. 1, as is well known in the art. In some cases, a peripheral device may be permanently or semi-permanently connected to computing unit 103. For example, with many computers, computing unit 103, hard disk drive 117, removable optical disk drive 119 and a display are semi-permanently encased in a single housing.

Still other peripheral devices may be removably connected to computer 101, however. Computer 101 may include, for example, one or more communication ports through which a peripheral device can be connected to computing unit 103 (either directly or indirectly through bus 113). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, computer 101 may include a wireless data "port," such as a Bluetooth® interface, a Wi-Fi interface, an infrared data port, or the like.

It should be appreciated that a computing device employed according to the various examples of the invention may include more components than computer 101 illustrated in FIG. 1, fewer components than computer 101, or a different combination of components than computer 101. Some implementations of the invention, for example, may employ one or more computing devices that are intended to have a very specific functionality, such as a digital music player or server computer. These computing devices may thus omit unnecessary peripherals, such as the network interface 115, removable optical disk drive 119, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

Turning now to FIG. 2, as described above, pupillometry system 200 computer system 206 (non-transitory computer-readable storage medium 208, processor 210, and display 210) and positioning device 214 having radiation source 216 and camera 218. It will be understood that in alternate examples computer system 206 can include any of the additional computer system components described above in reference to computer 101 (shown in FIG. 1). It will be further understood that in other alternate examples the camera and the radiation source can have separate positioning mechanisms and/or can be hand-held.

In the present example, radiation source 216 is in data communication with computer system 206 and the non-transitory computer-readable instructions include instructions for regulating an "on" state/"off" state and/or an intensity of the radiation source. In some examples, computer system 206 regulates or controls an intensity pattern for the radiation source (e.g., a constant intensity pattern, a fluctuating intensity pattern, etc.). The radiation source is configured to project a desired frequency of radiation (e.g., infrared, visible light, etc.). The radiation source is further configured to project radiation to one or more pupils of the patient. In some examples, the radiation source can project radiation into one or both pupils of the patient. In other examples, the system can include more than one radiation source for separately projecting light into each pupil. In even other examples, the radiation source can be regulated or controlled by an independent mechanism or an independent computer system (e.g., a second computer system, manual operation, etc.).

As shown in FIG. 2, camera 218 (e.g., a digital camera) is also in data communication with computer system 206. Computer system 206 can command camera 218 to capture image data and then collect and time-stamp image data captured by the camera. Accordingly, camera 218 is configured to capture image data of one or both of the patient's pupils (e.g., pupils of patient 204). In some examples, the camera captures image data of both pupils of the patient. In other examples, the system can include more than one camera for separately capturing image data of each pupil.

It be appreciated that the non-transitory computer-readable instructions can further include instructions for collecting image data according to the intensity pattern of the radiation source (e.g., on state, off state, fluctuating intensity, constant intensity, alternating radiation sources, etc.). For example, the computer system can operate the camera to start collecting image data for a specific period of time according to a time when the radiation source is turned on, turned, off, and/or when the intensity is fluctuated.

In one specific example, the computer system can illuminate both pupils and record the pupil diameter in one eye, then extinguish the light in the non-measured eye, causing pupillary dilation in both eyes. Pupillary unrest in the measured eye with both eyes illuminated can be measured, along with the magnitude of reflex pupillary dilation when one light is extinguished. Alternatively, the computer system can illuminate one pupil with visible light and record pupil diameter, then change the illumination to infrared, causing reflex pupil dilation, and continue capturing images using an infrared sensitive camera. Pupillary unrest in the measured eye under visible light can be measured, along with the magnitude of reflex pupillary dilation when the light is changed from visible to infrared.

Figure 5:
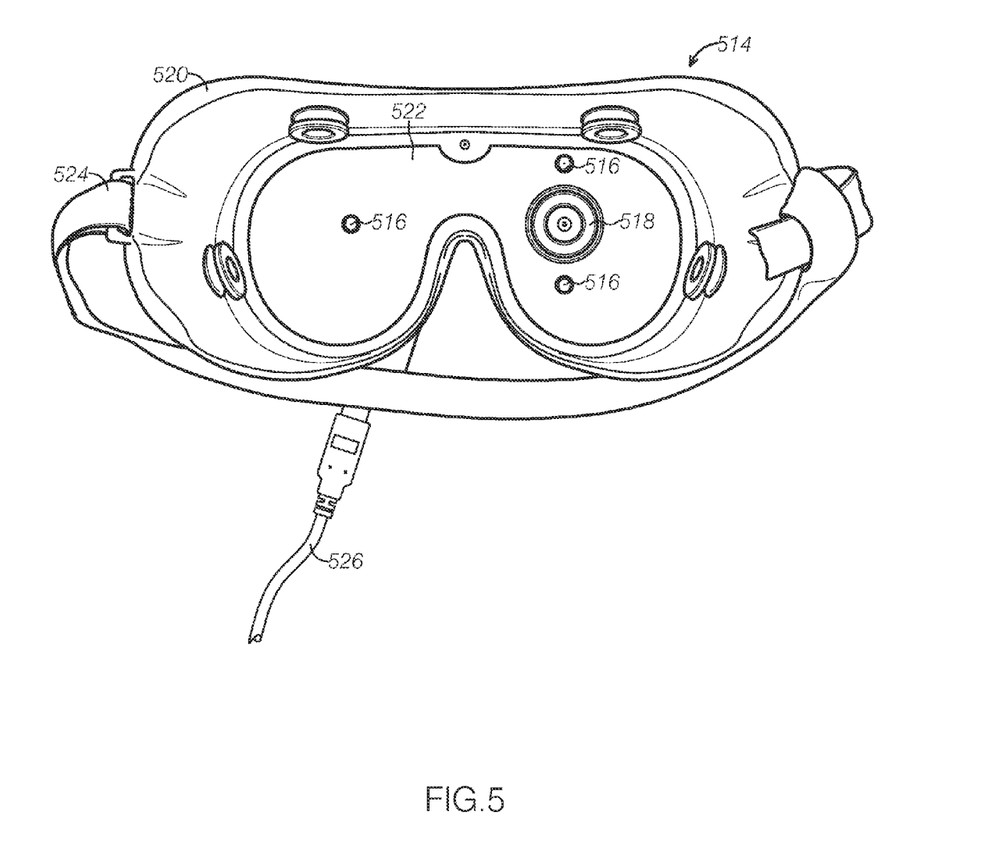
FIG. 5 front elevation view of a first example of a positioning device for the radiation source and the camera of the first example pupillometry system shown in FIG. 2.

In the example shown in FIG. 2, radiation source 216 and camera 218 are retained in a positioning mechanism 214. One specific example of a positioning mechanism, positioning mechanism 514, is shown in FIG. 5. In the example of FIG. 5, positioning mechanism 514 is a pair of goggles 520 having a camera 518 and radiation sources 516 mounted in a lens 522 of the goggles. Goggles 520 can be held to the patient's face and/or a strap 524 can be used to secure the goggles to the patient's head. A cable 526 is coupled to the computer system at a first end (not specifically shown) and to camera 518 and radiation sources 516 at a second end. Accordingly, the cable allows data communication between the camera and the radiation sources.

In alternate examples, the camera and the radiation source(s) can be retained and/or mounted in a different positioning mechanism (e.g., mounted on a stand, mounted on a flexible arm, mounted in a pair of glasses, etc.). In other alternate examples, the camera and the radiation source(s) can be retained and/or mounted on separate positioning mechanisms. In even other alternate examples, one or more of the camera and the radiation source(s) can be hand held.

Returning to FIG. 2, in addition to regulating an "on" state/"off" state and/or an intensity of the radiation source, commanding the camera to capture image data, and collecting and time-stamp image data, computer system 206 is configured to receive commands from operator 202, process the image data, and display the processed image data to the operator. An example method for operating the pupillometry system, method 300, is shown in FIG. 3, and an example method of operations carried out by the computer system, method 400, is shown in FIG. 4.

Figure 3:
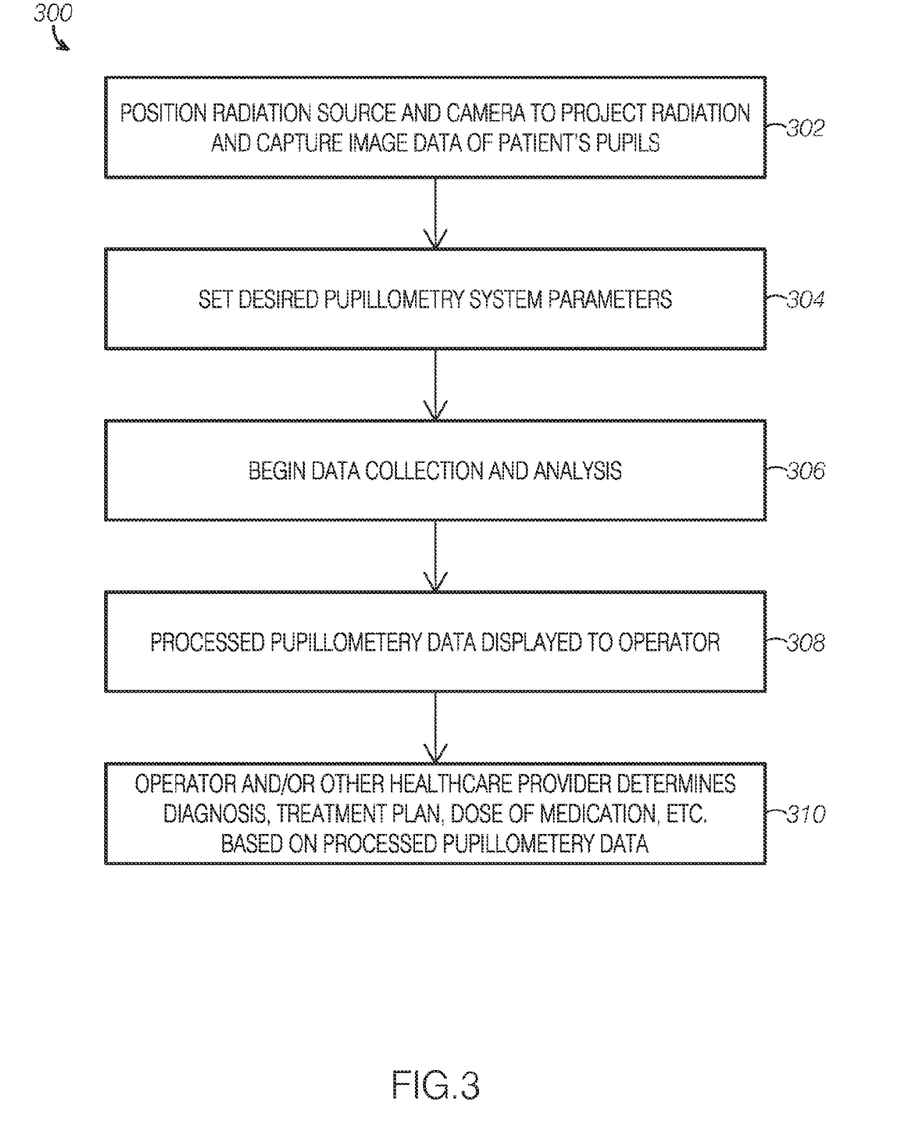
FIG. 3 is a flow diagram of a first example method for use of the first example pupillometry system shown in FIG. 2.
Figure 4:
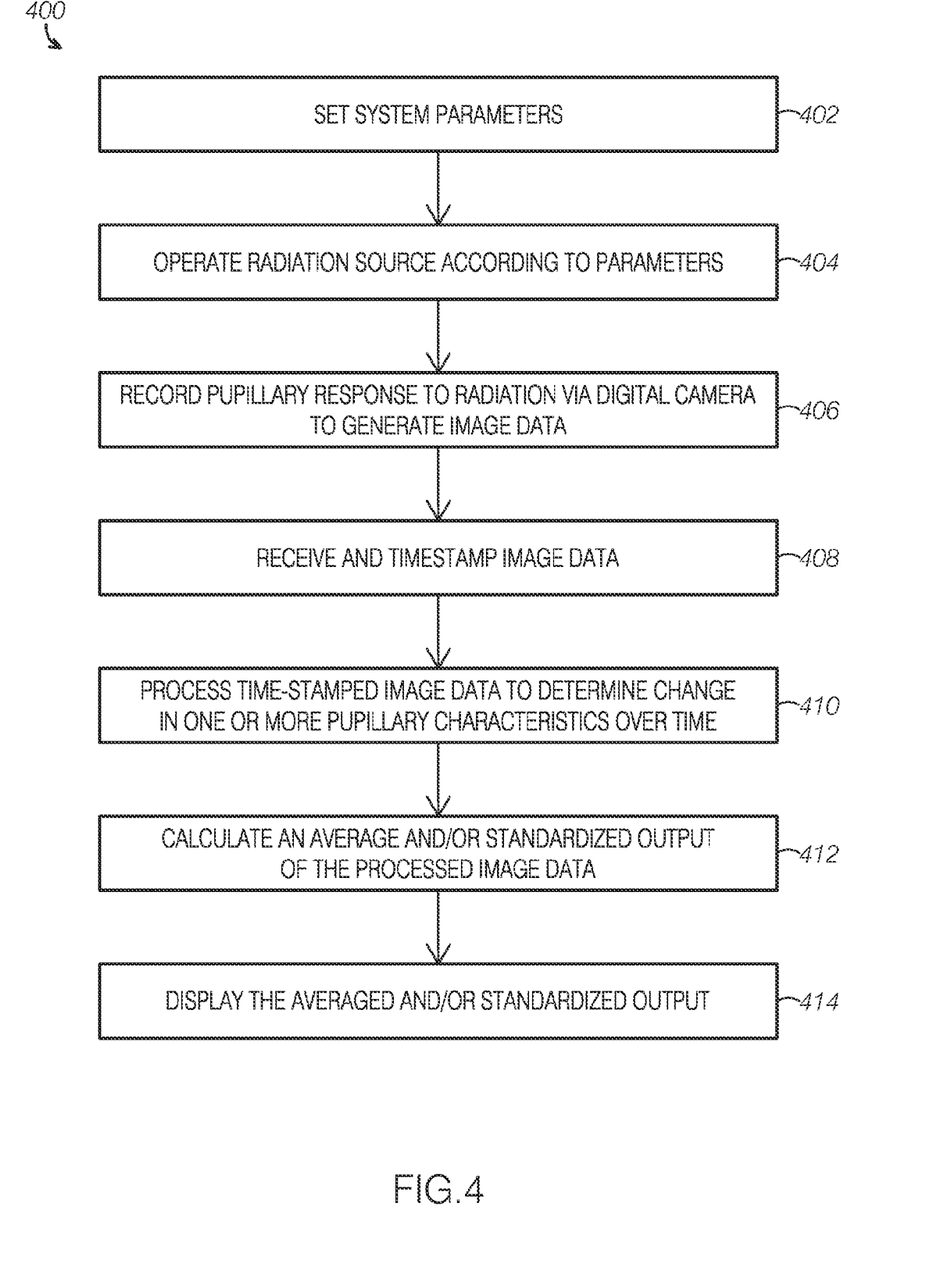
FIG. 4 is a flow diagram of computer-readable instructions for the non-transitory computer-readable storage medium for the first example pupillometry system shown in FIG. 2.

As depicted in FIG. 3, first at step 302, the radiation source(s) is positioned to project radiation into one or both eyes of the patient and the camera is positioned to capture image data of the pupils from one or both eyes of the patient. Next, the operator sets and/or programs the computer system with the desired parameters for data collection (e.g., radiation pattern, timing for image capture, duration of data collection, pupillary characteristics to be measured, etc.) at step 304. It will be appreciated that in alternate examples the parameters can be pre-set by the manufacturer (i.e., default settings). In these alternate examples, the operator can manually override and/or adjust the pre-set parameters.

The operator then commands the computer system to begin data collection and analysis according to the desired parameters at step 306. The processed pupillometry data is displayed to the operator at step 308. Finally, at step 310, the operator and/or another healthcare provider uses the pupillometry data to determine a diagnosis, treatment plan, prognosis, appropriate dose of a medication, etc. for the patient based on the processed pupillometry data. For example, pupillary unrest has been shown to be depressed by opioid pain medications. A patient with depressed pupillary unrest who continues to have pain may be less responsive to further opioid pain medications than other types of pain medication.

In order to perform image data capture, analysis, and display, the non-transitory computer-readable storage medium includes computer-readable instructions for: collecting and time stamping the image data, identifying and measuring the one or more pupils in the image data, processing the image data to produce measurement data of change in the one or more pupillary characteristics, and calculating a standardized output of measurement data for the one or more pupillary characteristics. As stated above, one example method of operations for the computer system, method 400, is shown in FIG. 4.

As depicted in FIG. 4, first at step 402, the computer system receives system parameters from the operator via a graphical user interface (GUI). In some examples, the parameters are set in a desired default mode for operation of the pupillometry system. In these examples, the default parameters may be adjustable and/or changeable by the operator as desired. System parameters can include one or more of radiation pattern (e.g., constant intensity, fluctuating intensities, alternating visible and infrared radiation, etc.), radiation type (e.g., visible light, infrared, etc.), rate of image capture, type of image capture (e.g., movie, still images, etc.), sampling period (i.e., duration of image data collection), pupillary characteristics to be measured (e.g., radius, diameter, circumference, absolute size, etc.), and/or measurement of one or both pupils.

Next, at step 404, the pupillometry system is operated according the system parameters. The pupillometry system then records the pupillary response to radiation using the digital camera to generate raw image data, and the image data is received and time stamped by the computer system at steps 406 and 408, respectively. In general, intrinsic pupil oscillations (i.e., the pupillary response to a constant intensity of radiation) are recorded. Additionally or alternatively, pupil reflex dilation (i.e., the pupillary response to fluctuations in light intensity) can be recorded. In even other examples, the pupillary response to exposure to a first radiation source (e.g., a visible light source) and then a second radiation source (e.g., an infrared light source) can be recorded.

At step 410, the time-stamped image data is processed. In some examples, where the camera is hand-held during data collection, processing of image data can include post-image processing to normalize pupil size and eliminate motion artifact of image data. For example, a line of the form d=mt+b can be fitted to the pupil diameter data, where d is the pupil diameter, t is time, and m and b are arbitrary constants. This can then be subtracted from the pupil diameter data, eliminating the constant and linearly increasing or decreasing components of the signal, and leaving only the pupillary unrest of interest.

In general, processing image data includes identification of the pupil in the images, measurement of the pupil (e.g., radius, diameter, circumference, absolute size, etc.), and plotting the magnitude of oscillations vs. time. The magnitude of oscillations within a clinically relevant frequency range are identified. For example, a frequency range of 0.2-2.5 Hz can be a clinically relevant frequency range. It will be appreciated that other example frequency ranges can include 0.1-3 Hz, 0-4 Hz, 0.5-2 Hz, etc.

In order to generate a clinically relevant reading, an average and/or standardized output (e.g., average, sum, ratio, etc.) of the processed image data is calculated at step 412. The data can be transformed via Fourier transform, Fast Fourier transform, or similar techniques such as detecting local minima and maxima in a given time period. Further, in some examples, an area under the curve of the transform in the range of the clinically relevant frequency range is calculated. Furthermore, in some examples, ratios of standardized output of different measurements can be calculated. Finally, the averaged and/or standardized output is displayed on a display of the computer system at step 414. In alternate examples, the computer system can additionally display an automated recommendation of diagnosis, treatment plan, prognosis, appropriate dose of a medication, etc. for the patient based on the processed pupillometry data.

In one specific example where the system is configured to measure intrinsic pupil oscillations in response to projection of the radiation source at a constant intensity, processing the image data to produce measurement data of change in one or more pupillary characteristics includes transforming measurement data via Fourier transform to produce measurements of amplitude of oscillation versus frequency. Further, in this example, calculating a standardized output of measurement data includes selecting a frequency region of interest and averaging amplitude in the frequency region of interest.

In a second specific example where the system is configured to measure intrinsic pupil oscillations in response to projection of the radiation source at a constant intensity, processing the image data to produce measurement data of change in the pupillary characteristics includes transformation of the pupillary characteristics over time into measurements of amplitude. Further, in this example, the measurements of amplitude are determined by identifying a maxima and a minima of the pupillary characteristics within a period of time.

In another specific example where the system is configured to measure pupil reflex dilation in response to projection of the radiation source at fluctuating intensities, processing the image data to produce measurement data of change in the pupillary characteristics includes determining oscillations in pupil size over time. Further, in this example, calculating a standardized output of measurement data for the pupillary characteristics includes determining absolute size change over time, percentage of change over time, amplitude of pupil oscillations, and/or ratio of absolute change over time to percentage of change over time.

In even another specific example, where the system is configured to measure intrinsic pupil oscillations and pupil reflex dilation, calculating a standardized output of measurement data for the pupillary characteristics includes calculating a ratio of a standardized value of intrinsic pupil oscillations to a standardized value of pupil reflex dilation. In other words, the measured pupillary response is the oscillations of pupil diameter that happen at steady state, that is, a constant amount of light. As a secondary measurement, the amount of light can be changed and the pupillary response recorded. The magnitude of the secondary measurement can be compared with the magnitude of the steady state oscillations. In this example, two separate phenomena are measured and two separate measurements, and both measurements, and their ratios, are presented to the operator.

Figure 6:
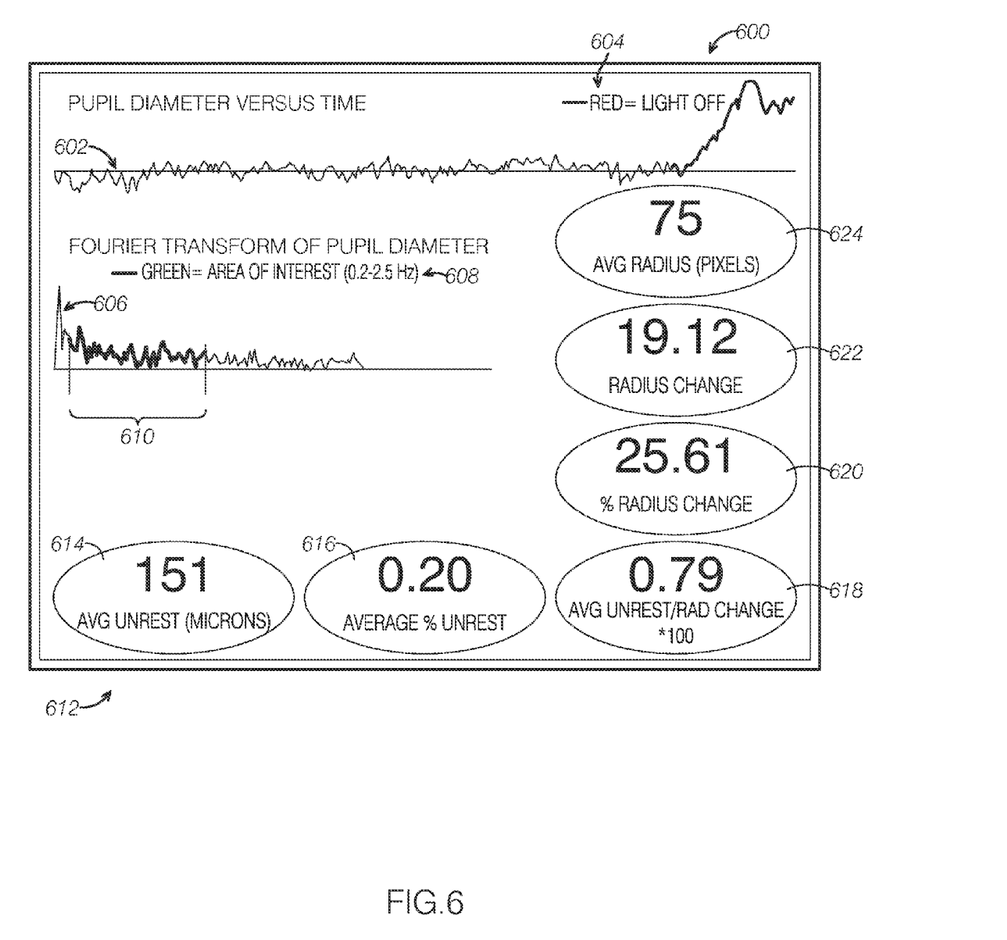
FIG. 6 a front elevation view of a first example data output screen from that can be displayed on the display of the first example pupillometry system shown in FIG. 2.

Turning now to FIG. 6, an example screen shot 600 that can be displayed on display 212 is shown. In the present example, graph 602 shows a raw measurement data of pupillary characteristic data (e.g., pupil diameter vs. time) and an indicator 604 indicates a coloration (e.g., red) of the graph where the radiation source was turned off. Graph 606 shows a Fourier transform of the raw measurement data and an indicator 608 indicates a coloration (e.g., green) of the graph that indicates a clinically relevant frequency range (e.g., 0.2-2.5 Hz). A range indicator 610 additionally identifies the clinically relevant frequency range.

Screen shot 600 further includes a plurality of averaged and/or standardized output readings 612. Specifically, plurality of averaged and/or standardized output readings 612 include an average unrest reading 614, an average percent unrest reading 616, an average unrest/radius change reading 618, a percent radius change reading 620, a radius change reading 622, and an average radius reading 624. It will be appreciated that the plurality of averaged and/or standardized output readings can include fewer or more readings. In one specific alternate example, the plurality of averaged and/or standardized output readings can additionally include the average pupil diameter in dark or light, or the average pupil to iris ratio in dark or light, time elapsed before pupil reaches a certain percentage of its final diameter when light level is changed, or other pupil data.

In summary, the use of Fourier transform and calculation of area under the curve in a relevant frequency is a useful and reliable method for analyzing pupillary response. In some situations, one might suppose that the relevant metric would be the high peak within some frequency range, or the number of peaks, or some other similar criteria. These criteria are, however, vulnerable to distortion caused by drift in the frequency of pupillary unrest and/or variation in frequency between individuals. Accordingly, these criteria are unreliable, whereas area under the curve is reliable.

In addition to the summation and display of the area under the curve, the pupillometry system may additionally test the response of the pupil to controlled light stimulus, and provide this as additional diagnostic information. The controlled light stimulus may take the form of a sine wave or other periodic function, or some other function, and the data measured can consist of both the changes in pupil diameter along with the time required for the pupil to reach its new diameter.

In one example of the presently described pupillometry system, the system applies a light stimulus at a certain level and then abruptly changes the light level. Concurrently, the system measures the magnitude of change in pupil diameter and the amount of time required for the pupil to change size. These quantities are then displayed, along with the area under the curve. Additionally, the ratio of these quantities to area under the curve can be displayed to assist the operator in interpreting the pupillometry data.

Lastly, in addition to the above measurements, the absolute size of the pupil can be measured to further assist in the interpretation of pupillometry data. The absolute pupil size can be displayed, along with the ratio of the area under the curve to absolute pupil size. The advantages of the present invention include, without limitation, the capability to provide the operator with detailed information on the pupillary unrest of the subject, as well as its magnitude in comparison to other pupil characteristics, with minimal effort or skill on the part of the operator.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinadons of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A pupillometry system for measuring one or more pupillary characteristics of a patient, comprising:
    at least one camera for capturing image data of one or more pupils of the patient;
    at least one radiation source configured to project radiation to the one or more pupils; and
    a computer system in data communication with the at least one camera, the computer system including a processor and a non-transitory computer-readable storage medium, the non-transitory computer-readable storage medium having instructions for:
        collecting and time stamping the image data,
        identifying and measuring the one or more pupils in the image data,
        processing the image data to produce measurement data of change in the one or more pupillary characteristics, and
        calculating a standardized output of measurement data for the one or more pupillary characteristics.

2. The pupillometry system of claim 1, further comprising a positioning mechanism configured to position the camera in an orientation to capture image data of the one or more pupils.

3. The pupillometry system of claim 2, wherein the positioning mechanism is further configured to position the at least one radiation source in an orientation to project radiation into the one or more pupils.

4. The pupillometry system of claim 1, wherein the at least one radiation source is configured to project one or more of visible light and infrared radiation.

5. The pupillometry system of claim 1, wherein the one or more pupillary characteristics are one or more of pupil radius, pupil diameter, pupil circumference, and absolute pupil size.

6. The pupillometry system of claim 1, wherein the computer system is in data communication with the radiation source, and
wherein the non-transitory computer-readable storage medium further has instructions for regulating an intensity pattern of the radiation source and collecting image data according to the intensity pattern.

7. The pupillometry system of claim 1, wherein the system is configured to measure intrinsic pupil oscillations in response to projection of the radiation source at a constant intensity.

8. The pupillometry system of claim 7, wherein processing the image data to produce measurement data of change in the one or more pupillary characteristics comprises transforming measurement data via Fourier transform to produce measurements of amplitude of oscillation versus frequency.

9. The pupillometry system of claim 8, wherein calculating a standardized output of measurement data for the one or more pupillary characteristics comprises selecting a frequency region of interest and then calculating one or more of an average and a sum of a height of amplitude in the frequency region of interest.

10. The pupillometry system of claim 7, wherein processing the image data to produce measurement data of change in the one or more pupillary characteristics comprises transformation of the one or more pupillary characteristics over time into measurements of amplitude, and
wherein the measurements of amplitude are determined by identifying a maxima of the one or more pupillary characteristics and a minima of the one or more pupillary characteristics within a period of time.

11. The pupillometry system of claim 1, wherein the system is configured to measure pupil reflex dilation in response to projection of the radiation source at fluctuating intensities.

12. The pupillometry system of claim 11, wherein processing the image data to produce measurement data of change in the one or more pupillary characteristics comprises determining oscillations in pupil size over time.

13. The pupillometry system of claim 12, wherein calculating a standardized output of measurement data for the one or more pupillary characteristics comprises determining one or more of absolute size change over time, percentage of change over time, amplitude of pupil oscillations, and ratio of absolute change over time to percentage of change over time.

14. The puillometry system of claim 1, wherein the system is configured to measure intrinsic pupil oscillations and pupil reflex dilation, and
wherein calculating a standardized output of measurement data for the one or more pupillary characteristics comprises calculating a ratio of a standardized value of intrinsic pupil oscillations to a standardized value of pupil reflex dilation.

15. The pupillometry system of claim 1, wherein the non-transitory computer-readable storage medium further has instructions for post-image processing to normalize pupil size and eliminate motion artifact of image data.

16. A pupillometry system for measuring one or more pupillary characteristics of a patient, the one or more pupillary characteristics comprising one or more of pupil radius, pupil diameter, pupil circumference, absolute pupil size, and pupil to iris ratio, the pupillometry system comprising:
at least one camera for capturing image data of one or more pupils of the patient;
at least one radiation source configured to project radiation to the one or more pupils; and
a computer system in data communication with the at least one camera and the at least one radiation source, the computer system including a processor, a display, and a non-transitory computer-readable storage medium, the non-transitory computer-readable storage medium having instructions for:
regulating an intensity pattern of the radiation source,
collecting image data according to the intensity pattern of the radiation source,
time stamping the image data,
identifying and measuring the one or more pupils in the image data,
processing the image data to produce measurement data of change in the one or more pupillary characteristics,
calculating a standardized output of measurement data of the one or more pupillary characteristics, and
displaying the standardized output on the display.

17. The pupillometry system of claim 16, wherein the system is configured to measure intrinsic pupil oscillations in response to projection of the radiation source at a constant intensity,
wherein processing the image data to produce measurement data of change in the one or more pupillary characteristics comprises transforming measurement data via Fourier transform to produce measurements of amplitude of oscillation versus frequency, and
wherein calculating a standardized output of measurement data for the one or more pupillary characteristics comprises selecting a frequency region of interest and then calculating one or more of an average and a sum of a height of amplitude in the frequency region of interest.

18. The pupillometry system of claim 16, wherein the system is configured to measure pupil reflex dilation in response to projection of the radiation source at fluctuating intensities,
wherein processing the image data to produce measurement data of change in the one or more pupillary characteristics comprises determining oscillations in pupil size over time, and
wherein calculating a standardized output of measurement data for the one or more pupillary characteristics comprises determining one or more of absolute size change over time, percentage of change over time, amplitude of pupil oscillations, and ratio of absolute change over time to percentage of change over time.

19. A pupillometry system for measuring one or more pupillary characteristics of a patient, the system comprising:
at least one camera for capturing image data of one or more pupils of the patient;
at least one radiation source configured to project radiation to the one or more pupils, the radiation being one or more of visible light and infrared radiation; and
a computer system in data communication with the measurement device, the computer system including a processor and a non-transitory computer-readable storage medium, the non-transitory computer-readable storage medium having instructions for:
regulating an intensity pattern of the radiation source,
collecting image data according to the intensity pattern,
time stamping the image data,
identifying and measuring the one or more pupils in the image data,
processing the image data to produce measurement data of change in the one or more pupillary characteristics over time, and
calculating a standardized output of measurement data of the one or more pupillary characteristics,
wherein the system is configured to measure intrinsic pupil oscillations in response to projection of the radiation source at a constant intensity, and
wherein, in response to projection of the radiation source at a constant intensity, processing the image data to produce measurement data of change in the one or more pupillary characteristics over time comprises transforming measurement data via Fourier transform to produce measurements of amplitude of oscillation versus frequency, and calculating a standardized output of measurement data of the one or more pupillary characteristics comprises selecting a frequency region of interest and averaging a height of amplitude in the frequency region of interest.

20. The pupillometry system of claim 19, wherein the system is further configured to measure pupil reflex dilation in response to projection of the radiation source at fluctuating intensities,
wherein calculating a standardized output of measurement data of the one or more pupillary characteristics comprises determining one or more of absolute size change over time, percentage of change over time, amplitude of pupil oscillations, and ratio of absolute change over time to percentage of change over time, and
wherein the non-transitory computer-readable storage medium further includes instructions for calculating a ratio of a standardized value of intrinsic pupil oscillations to a standardized value of pupil reflex dilation.

* * * * *